US010603481B2

(12) United States Patent
Avula et al.

(10) Patent No.: US 10,603,481 B2
(45) Date of Patent: Mar. 31, 2020

(54) DISINFECTING LUER CAP AND METHOD OF USE

(71) Applicant: Merit Medical Systems, Inc., South Jordan, UT (US)

(72) Inventors: Mahender Avula, South Jordan, UT (US); Richard P. Jenkins, Bluffdale, UT (US); Kenneth Sykes, Bluffdale, UT (US); Robert Hitchcock, Salt Lake City, UT (US); F. Mark Ferguson, Salt Lake City, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 133 days.

(21) Appl. No.: 15/874,505

(22) Filed: Jan. 18, 2018

(65) Prior Publication Data
US 2018/0214684 A1  Aug. 2, 2018

Related U.S. Application Data

(60) Provisional application No. 62/560,808, filed on Sep. 20, 2017, provisional application No. 62/451,298, filed on Jan. 27, 2017.

(51) Int. Cl.
*A61M 5/31* (2006.01)
*A61M 25/16* (2006.01)
(Continued)

(52) U.S. Cl.
CPC .............. *A61M 39/162* (2013.01); *A61L 2/18* (2013.01); *A61L 2/186* (2013.01); *A61M 39/10* (2013.01);
(Continued)

(58) Field of Classification Search
CPC .. A61L 2202/123; A61L 2/18; A61M 39/162; A61M 39/20; A61M 39/10;
(Continued)

(56) References Cited

U.S. PATENT DOCUMENTS 1,744,026 A  10/1926  Baltzley
1,868,200 A  7/1932  Freedman
(Continued)

FOREIGN PATENT DOCUMENTS

CN  205549223  9/2016
EP  0229786  7/1987
(Continued)

OTHER PUBLICATIONS

International Search Report and Written Opinion dated Jan. 24, 2019 for PCT/US2018/054202.
(Continued)

*Primary Examiner* — Rebecca E Eisenberg
(74) *Attorney, Agent, or Firm* — Stoel Rives LLP

(57) ABSTRACT

Medical devices including a cap for a medical connector are disclosed. In some embodiments, the cap comprises a disinfectant, such as an antiseptic fluid and an insert configured to seal or partially seal the medical connector as it is engaged with the cap. In some embodiments the cap insert has a segment which is deformable under axially applied pressure as an end-user attaches the cap to the medical connector. In some embodiments this insert is configured to improve the exposure of antiseptic to the outer surface of the medical connector while minimizing exposure of the antiseptic inside the medical connector open lumen.

19 Claims, 9 Drawing Sheets

(51) Int. Cl.
  *A61M 25/18* (2006.01)
  *A61M 39/16* (2006.01)
  *A61M 39/10* (2006.01)
  *A61L 2/18* (2006.01)
  *A61M 39/20* (2006.01)
  *A61B 18/00* (2006.01)
  *A61B 18/14* (2006.01)

(52) U.S. Cl.
  CPC ......... *A61M 39/20* (2013.01); *A61B 18/1492* (2013.01); *A61B 2018/00178* (2013.01); *A61L 2202/123* (2013.01); *A61L 2202/24* (2013.01); *A61M 2039/1038* (2013.01)

(58) Field of Classification Search
  CPC .... A61M 39/165; A61M 39/16; A61M 39/18; A61M 35/006
  See application file for complete search history.

(56) References Cited

U.S. PATENT DOCUMENTS

| | | | |
|---|---|---|---|
| 2,356,969 A | 5/1942 | Blum |
| 2,299,037 A | 10/1942 | Saueressig |
| 2,351,804 A | 6/1944 | Blum |
| 3,315,830 A | 4/1967 | Flynn |
| 3,431,548 A | 3/1969 | Busler |
| 3,446,596 A | 5/1969 | Salivar et al. |
| 3,976,311 A | 8/1976 | Spendlove |
| 3,987,930 A | 10/1976 | Fuson |
| 4,121,727 A | 10/1978 | Robbins et al. |
| 4,232,677 A | 11/1980 | Leibinsohn |
| 4,299,330 A | 11/1981 | Walter |
| 4,324,239 A | 4/1982 | Gordon et al. |
| 4,334,551 A | 6/1982 | Pfister |
| 4,344,551 A | 6/1982 | Pfister |
| 4,340,052 A | 7/1982 | Dennehey et al. |
| 4,346,703 A | 8/1982 | Dennehey et al. |
| 4,354,490 A | 10/1982 | Rogers |
| 4,369,781 A | 1/1983 | Gilson et al. |
| 4,402,691 A | 9/1983 | Rosenthal et al. |
| 4,432,764 A | 2/1984 | Lopez |
| 4,432,766 A | 2/1984 | Bellotti et al. |
| 4,440,207 A | 4/1984 | Genatempo et al. |
| 4,450,624 A | 5/1984 | Collier |
| 4,572,373 A | 2/1986 | Johansson |
| 4,597,758 A | 7/1986 | Aalto et al. |
| 4,624,664 A | 11/1986 | Peluso et al. |
| 4,667,837 A | 5/1987 | Vitello et al. |
| 4,671,306 A | 6/1987 | Spector |
| 4,778,447 A | 10/1988 | Velde et al. |
| 4,798,303 A | 1/1989 | Arnold |
| 4,810,241 A | 3/1989 | Rogers |
| 4,838,875 A | 6/1989 | Somor |
| D303,631 S | 9/1989 | Demarest |
| D310,542 S | 9/1990 | Regnault |
| 4,991,629 A | 2/1991 | Ernesto et al. |
| 5,006,114 A | 4/1991 | Rogers et al. |
| 5,184,742 A | 2/1993 | DeCaprio et al. |
| D333,788 S | 3/1993 | Geschwender |
| 5,190,534 A | 3/1993 | Kendell |
| 5,195,957 A | 3/1993 | Tollini |
| 5,205,821 A | 4/1993 | Kruger et al. |
| 5,242,425 A | 9/1993 | White et al. |
| D340,112 S | 10/1993 | Zeman |
| D341,227 S | 11/1993 | Lang et al. |
| 5,269,771 A | 12/1993 | Thomas et al. |
| 5,385,372 A | 1/1995 | Utterberg |
| 5,439,451 A | 8/1995 | Collinson et al. |
| 5,445,270 A | 8/1995 | Dratz |
| 5,451,113 A | 9/1995 | Lund et al. |
| 5,466,219 A | 11/1995 | Lynn et al. |
| 5,492,147 A | 2/1996 | Challender et al. |
| 5,536,258 A | 7/1996 | Folden |
| 5,554,135 A | 9/1996 | Menyhay |
| 5,620,427 A * | 4/1997 | Werschmidt .......... A61M 39/10 137/516.13 |
| 5,694,978 A | 12/1997 | Heilmann et al. |
| 5,702,017 A | 12/1997 | Goncalves |
| 5,738,663 A | 4/1998 | Lopez |
| 5,792,120 A | 8/1998 | Menyhay |
| 5,894,015 A | 4/1999 | Rechtin |
| 5,951,519 A | 9/1999 | Utterberg |
| 5,954,657 A | 9/1999 | Rados |
| 5,954,957 A | 9/1999 | Chin-Loy et al. |
| 6,045,539 A | 4/2000 | Menyhay |
| 6,152,913 A | 11/2000 | Feith et al. |
| 6,171,287 B1 | 1/2001 | Lynn et al. |
| D456,668 S | 5/2002 | Tse |
| D468,015 S | 12/2002 | Horppu |
| D470,888 S | 2/2003 | Kuboshima |
| 6,523,686 B1 | 2/2003 | Bae |
| 6,932,795 B2 | 8/2005 | Lopez et al. |
| 6,960,191 B2 | 11/2005 | Howlett et al. |
| 7,014,169 B2 | 3/2006 | Newton et al. |
| 7,040,598 B2 | 5/2006 | Raybuck |
| 7,040,669 B2 | 5/2006 | Kenmotsu et al. |
| 7,198,611 B2 | 4/2007 | Connell et al. |
| D545,964 S | 7/2007 | Blanco |
| D547,446 S | 7/2007 | Racz et al. |
| D550,355 S | 9/2007 | Racz et al. |
| 7,282,186 B2 | 10/2007 | Lake, Jr. et al. |
| 7,316,669 B2 | 1/2008 | Ranalletta |
| D573,643 S | 7/2008 | Brigham et al. |
| D607,325 S | 1/2010 | Rogers et al. |
| 7,762,524 B2 | 7/2010 | Cawthon et al. |
| 7,762,988 B1 | 7/2010 | Vitello |
| 7,763,006 B2 | 7/2010 | Tennican |
| 7,780,794 B2 | 8/2010 | Rogers et al. |
| D632,574 S | 2/2011 | Huntington et al. |
| 7,922,701 B2 | 4/2011 | Buchman |
| D639,421 S | 6/2011 | Sano et al. |
| 7,985,302 B2 | 7/2011 | Rogers et al. |
| 8,167,847 B2 | 5/2012 | Anderson et al. |
| 8,172,825 B2 | 5/2012 | Solomon et al. |
| 8,177,761 B2 | 5/2012 | Howlett et al. |
| 8,197,749 B2 | 6/2012 | Howlett et al. |
| 8,231,587 B2 | 7/2012 | Solomon et al. |
| 8,231,602 B2 | 7/2012 | Anderson et al. |
| 8,273,303 B2 | 9/2012 | Ferlic et al. |
| 8,328,767 B2 | 12/2012 | Solomon et al. |
| 8,343,112 B2 | 1/2013 | Solomon et al. |
| 8,419,713 B1 | 4/2013 | Solomon et al. |
| 8,523,830 B2 | 9/2013 | Solomon et al. |
| 8,523,831 B2 * | 9/2013 | Solomon .............. A61M 39/162 220/380 |
| 8,641,681 B2 | 2/2014 | Solomon et al. |
| 8,647,308 B2 | 2/2014 | Solomon et al. |
| 8,647,326 B2 | 2/2014 | Solomon et al. |
| 8,740,864 B2 | 6/2014 | Hoang |
| 8,784,388 B2 | 7/2014 | Charles et al. |
| 8,808,637 B2 | 8/2014 | Ferlic |
| 8,961,475 B2 | 2/2015 | Solomon et al. |
| 9,079,692 B2 | 7/2015 | Solomon et al. |
| 9,101,750 B2 | 8/2015 | Solomon et al. |
| 9,114,915 B2 | 8/2015 | Solomon et al. |
| 9,242,084 B2 | 1/2016 | Solomon et al. |
| 9,352,140 B2 | 5/2016 | Kerr et al. |
| 2002/0093192 A1 | 7/2002 | Matkovich |
| 2003/0140441 A1 | 7/2003 | Stafford |
| 2003/0153865 A1 | 8/2003 | Connell et al. |
| 2003/0181849 A1 | 9/2003 | Castellanos |
| 2003/0198502 A1 | 10/2003 | Maloney et al. |
| 2004/0039341 A1 | 2/2004 | Ranalletta |
| 2004/0195136 A1 | 10/2004 | Young et al. |
| 2004/0201216 A1 | 10/2004 | Segal et al. |
| 2004/0214316 A1 | 10/2004 | O'Connell |
| 2004/0258560 A1 | 12/2004 | Lake, Jr. et al. |
| 2005/0033267 A1 | 2/2005 | Decaria |
| 2005/0038397 A1 | 2/2005 | Newton et al. |
| 2005/0124970 A1 | 6/2005 | Kunin et al. |
| 2005/0147524 A1 | 7/2005 | Bousquet |
| 2005/0183971 A1 | 8/2005 | Petricca |
| 2005/0203460 A1 | 9/2005 | Kim |

(56) References Cited

U.S. PATENT DOCUMENTS

| | | |
|---|---|---|
| 2005/0245883 A1 | 11/2005 | Baldwin |
| 2005/0265773 A1 | 12/2005 | De Laforcade |
| 2005/0266714 A1 | 12/2005 | Higgins et al. |
| 2006/0030827 A1 | 2/2006 | Raulerson et al. |
| 2006/0177250 A1 | 8/2006 | Nakagaki |
| 2007/0112333 A1 | 5/2007 | Hoang et al. |
| 2007/0202177 A1 | 8/2007 | Hoang |
| 2007/0282280 A1 | 12/2007 | Tennican |
| 2007/0287989 A1 | 12/2007 | Crawford et al. |
| 2007/0293818 A1 | 12/2007 | Stout et al. |
| 2007/0293822 A1 | 12/2007 | Crawford et al. |
| 2008/0019889 A1 | 1/2008 | Rogers et al. |
| 2008/0021381 A1 | 1/2008 | Lurvey |
| 2008/0027399 A1 | 1/2008 | Harding et al. |
| 2008/0033371 A1 | 2/2008 | Updefraff et al. |
| 2008/0038167 A1 | 2/2008 | Lynn |
| 2008/0039803 A1 | 2/2008 | Lynn |
| 2008/0097407 A1 | 2/2008 | Plishka |
| 2008/0086091 A1 | 4/2008 | Anderson et al. |
| 2008/0095680 A1 | 4/2008 | Steffens et al. |
| 2008/0105704 A1 | 5/2008 | Pritchard |
| 2008/0107564 A1 | 5/2008 | Sternberg et al. |
| 2008/0132880 A1 | 6/2008 | Buchman |
| 2008/0147047 A1 | 6/2008 | Davis et al. |
| 2008/0177250 A1 | 7/2008 | Howlett et al. |
| 2008/0190485 A1 | 8/2008 | Guala |
| 2008/0235888 A1 | 10/2008 | Vaillancourt et al. |
| 2009/0008393 A1 | 1/2009 | Howlett et al. |
| 2009/0062766 A1 | 3/2009 | Howlett et al. |
| 2009/0099529 A1 | 4/2009 | Anderson et al. |
| 2009/0149819 A1 | 6/2009 | Chelak |
| 2009/0205151 A1 | 8/2009 | Fisher et al. |
| 2010/0003067 A1 | 1/2010 | Shaw et al. |
| 2010/0047123 A1 | 2/2010 | Solomon et al. |
| 2010/0049170 A1 | 2/2010 | Solomon et al. |
| 2010/0063482 A1 | 3/2010 | Mansour et al. |
| 2010/0100056 A1 | 4/2010 | Cawthon et al. |
| 2010/0242993 A1 | 9/2010 | Hoang et al. |
| 2010/0306938 A1 | 12/2010 | Rogers et al. |
| 2010/0313366 A1 | 12/2010 | Rogers et al. |
| 2011/0044850 A1 | 2/2011 | Solomon et al. |
| 2011/0054440 A1 | 3/2011 | Lewis |
| 2011/0064512 A1 | 3/2011 | Shaw et al. |
| 2011/0165020 A1 | 7/2011 | Truggvason |
| 2011/0213341 A1 | 9/2011 | Solomon et al. |
| 2011/0217212 A1 | 9/2011 | Solomon et al. |
| 2011/0232020 A1 | 9/2011 | Rogers et al. |
| 2011/0277788 A1 | 11/2011 | Rogers et al. |
| 2011/0314619 A1 | 12/2011 | Schweikert |
| 2012/0016318 A1 | 1/2012 | Hoang et al. |
| 2012/0039764 A1 | 2/2012 | Solomon |
| 2012/0039765 A1 | 2/2012 | Solomon |
| 2012/0082977 A1* | 4/2012 | Rajagopal ............... B01L 3/508 435/6.1 |
| 2012/0216359 A1 | 8/2012 | Rogers et al. |
| 2013/0019421 A1* | 1/2013 | Rogers ................... B08B 1/001 15/104.93 |
| 2013/0072908 A1 | 3/2013 | Solomon et al. |
| 2013/0171030 A1 | 7/2013 | Ferlic et al. |
| 2013/0197485 A1 | 8/2013 | Gardner et al. |
| 2014/0010481 A1 | 1/2014 | Last et al. |
| 2014/0135739 A1 | 5/2014 | Solomon et al. |
| 2014/0227144 A1 | 8/2014 | Becton Dickson |
| 2015/0231384 A1 | 8/2015 | Ma et al. |
| 2015/0273199 A1 | 10/2015 | Adams et al. |
| 2015/0374968 A1 | 12/2015 | Solomon et al. |
| 2016/0038701 A1 | 2/2016 | White et al. |
| 2016/0045629 A1 | 2/2016 | Gardner et al. |
| 2016/0106968 A1 | 4/2016 | Solomon et al. |
| 2017/0245618 A1* | 8/2017 | Chen ................... A45D 34/045 |
| 2019/0099593 A1 | 4/2019 | Avula et al. |
| 2019/0209781 A1 | 7/2019 | Solomon et al. |

FOREIGN PATENT DOCUMENTS

| | | |
|---|---|---|
| EP | 0462355 | 12/1991 |
| JP | 64002760 | 1/1989 |
| WO | 2004035245 | 4/2004 |
| WO | 2006099306 A2 | 9/2006 |
| WO | 2008089196 A2 | 7/2008 |
| WO | 2008100950 A2 | 8/2008 |
| WO | 2010002808 A1 | 1/2010 |
| WO | 2010141508 A1 | 12/2010 |
| WO | 2011141508 | 12/2010 |
| WO | 2011053924 A1 | 5/2011 |
| WO | 2011066565 A1 | 6/2011 |
| WO | 2011066586 A1 | 6/2011 |
| WO | 2013184716 | 12/2013 |
| WO | 2015174953 | 11/2015 |

OTHER PUBLICATIONS

International Search Report and Written Opinion dated Feb. 1, 2017 for PCT/US2016/062061.
International Search Report and Written Opinion dated Jun. 22, 2018 for PCT/US2018/014237.
Office Action dated Apr. 26, 2018 for U.S. Appl. No. 14/797,533.
Office Action dated Jun. 7, 2018 for U.S. Appl. No. 14/947,341.
Office Action dated Mar. 27, 2019 for U.S. Appl. No. 14/797,533.
European Search Report dated Mar. 6, 2012 for EP08727689.5.
European Search Report dated Jun. 20, 2017 for EP10827614.8.
International Search Report and the Written Opinion dated Jan. 26, 2011 for PCT/US2010/058404.
International Search Report and Written Opinion dated Jan. 6, 2011 for PCT/US2010/054995.
International Search Report and Written Opinion dated Feb. 7, 2011 for PCT/US2010/058453.
International Search Report and Written Opinion dated Aug. 1, 2008 for PCT/US2008/051087.
International Search Report with Written Opinion dated Aug. 31, 2009 for PCT/US2009/049094.
Notice of Allowance dated Jun. 7, 2017 for U.S. Appl. No. 14/162,207.
Notice of Allowance dated Sep. 1, 2017 for U.S. Appl. No. 14/162,207.
Office Action dated Jan. 27, 2010 for U.S. Appl. No. 12/014,388.
Office Action dated Feb. 27, 2018 for U.S. Appl. No. 14/978,925.
Office Action dated Apr. 4, 2018 for U.S. Appl. No. 14/845,004.
Office Action dated Apr. 22, 2011 for U.S. Appl. No. 12/164,310.
Office Action dated May 5, 2009 for U.S. Appl. No. 12/014,388.
Office Action dated May 25, 2018 for U.S. Appl. No. 15/203,002.
Office Action dated Jun. 9, 2011 for U.S. Appl. No. 12/171,997.
Office Action dated Jun. 21, 2010 for U.S. Appl. No. 12/014,388.
Office Action dated Aug. 16, 2010 for U.S. Appl. No. 12/164,310.
Office Action dated Oct. 20, 2017 for U.S. Appl. No. 15/203,002.
Office Action dated Nov. 17, 2017 for U.S. Appl. No. 14/845,004.
Office Action dated Dec. 23, 2010 for U.S. Appl. No. 12/014,388.
Baxa Corporation Launches PadLock Set Saver for IV Safety press release, 2 pages, available at http://www.pr.com/press-release/55432. ,Oct. 10, 2007.
Baxa Corporation Padlock catalog, 3 pages, copyright 2009, available at http://www.baxa.com/SearchResults/ProductDetail/?id=6452BFB9-3048-7B87-701697FB93902BA6.
Baxa Corporation Padlock Microbial Testing Technical Paper, copyright 2007, 4 pages, available at http://www.baxa.com/resources/docs/technicalPapers/PadLockMicrobialChallengeTechPaper.pdf.
Baxa Corporation PadLock Set Saver Specifications and Instructions for Use, copyright 2007, 2 pages, available at http://www.baxa.com/resources/docs/5300103905C.pdf.
BD Q-Syte Luer Access Split Septum product brochure, 4 pages, available at http://www.bd.com/infusion/pdfs/D16333.pdf. ,Nov. 2008.
Braun product catalog, 2pages. ,Aug. 2008.
Curos Port Protector, web page from http://www.iveramed.com/, Jul. 11, 2008.
Curos Port Protector product brochure, 2 pages, available at http://www.iveramed.com/clocs/Curos%20Brochure-FINAL.pdf. ,Nov. 2008.

(56) References Cited

OTHER PUBLICATIONS

Hospira Male/Female Sterile Cap product packaging insert and brochure, 2 pages. ,Aug. 2004.

Kippmed Vented Non-Vented Female Luer Lock Caps, The KippGroup, ,Jan. 1995 ,2 pgs.

Tego Connector product brochure, 2 pages, available at http://www.icumed.com/Docs-Tego/M1-1148%20TEG0%20Folder%20Brochure%20Rev.3.pdf. ,Nov. 2008.

Unomedical Medical Products catalog, 2 pages, available at http://www.unomedical.net/au/section05/section10/LocalSSI/..%5C..%5Cpdf%5Cmedical.pdf ,Jan. 2006.

Buchman, et al.,A New Central Venous Catheter Cap: Decreased Microbial Growth and Risk for Catheter-Related Bloodstream Infection, The Journal of Vascular Access , ,Nov. 21, 2009.

Maki, et al., In Vitro Studies of a Novel Antimicrobial LuerActivated Needleless Connector for Prevention of Catheter-Related Blookstream Infection, Clinical Infection Diseases, vol. 50, Issue 12, Jun. 15, 2010 ,1580-1587.

Menyhay, et al.,Disinfection of Needleless Catheter Connecors and Access Ports with Alcohol May Not Prevent Microbial Entry: The Promise of a Novel Antiseptic-Barrier Cap, Infection control and Hospital Epidemiology, vol. 27 No. 1 ,Jan. 2006 ,23-27.

Stoker, et al.,One Less Problem, Safe Practrices when Administering IV Therapy, Managing Infection Control, 4 pgs ,Jun. 2008.

Notice of Allowance dated Sep. 17, 2018 for U.S. Appl. No. 14/845,004.

Notice of Allowance dated Oct. 25, 2018 for U.S. Appl. No. 14/947,341.

Notice of Allowance dated Nov. 9, 2018 for U.S. Appl. No. 15/203,002.

Office Action dated Sep. 14, 2018 for U.S. Appl. No. 14/978,925.

Office Action dated Nov. 29, 2018 for U.S. Appl. No. 14/797,533.

Office Action dated Aug. 30, 2019 for U.S. Appl. No. 15/979,213.

European Search Report dated Jun. 13, 2019 for EP16866954.7.

Office Action dated Jun. 3, 2019 for U.S. Appl. No. 14/978,925.

Office Action dated Jul. 17, 2019 for U.S. Appl. No. 14/797,533.

\* cited by examiner

DISINFECTING LUER CAP AND METHOD OF USE

RELATED APPLICATIONS

This application claims priority to U.S. Provisional Application No. 62/560,808, filed on Sep. 20, 2017 and titled, "Disinfecting Luer Cap and Method of Use," and U.S. Provisional Application No. 62/451,298, filed on Jan. 27, 2017 and titled, "Disinfecting Caps for Open Luer Connectors," both of which are hereby incorporated by reference in their entireties.

TECHNICAL FIELD

The field of the present disclosure relates generally to medical devices. More specifically, the present disclosure relates to caps for medical connectors. In some embodiments, the present disclosure relates to caps that can be used to protect the sterility of open medical connectors.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

DETAILED DESCRIPTION

Figure 1:
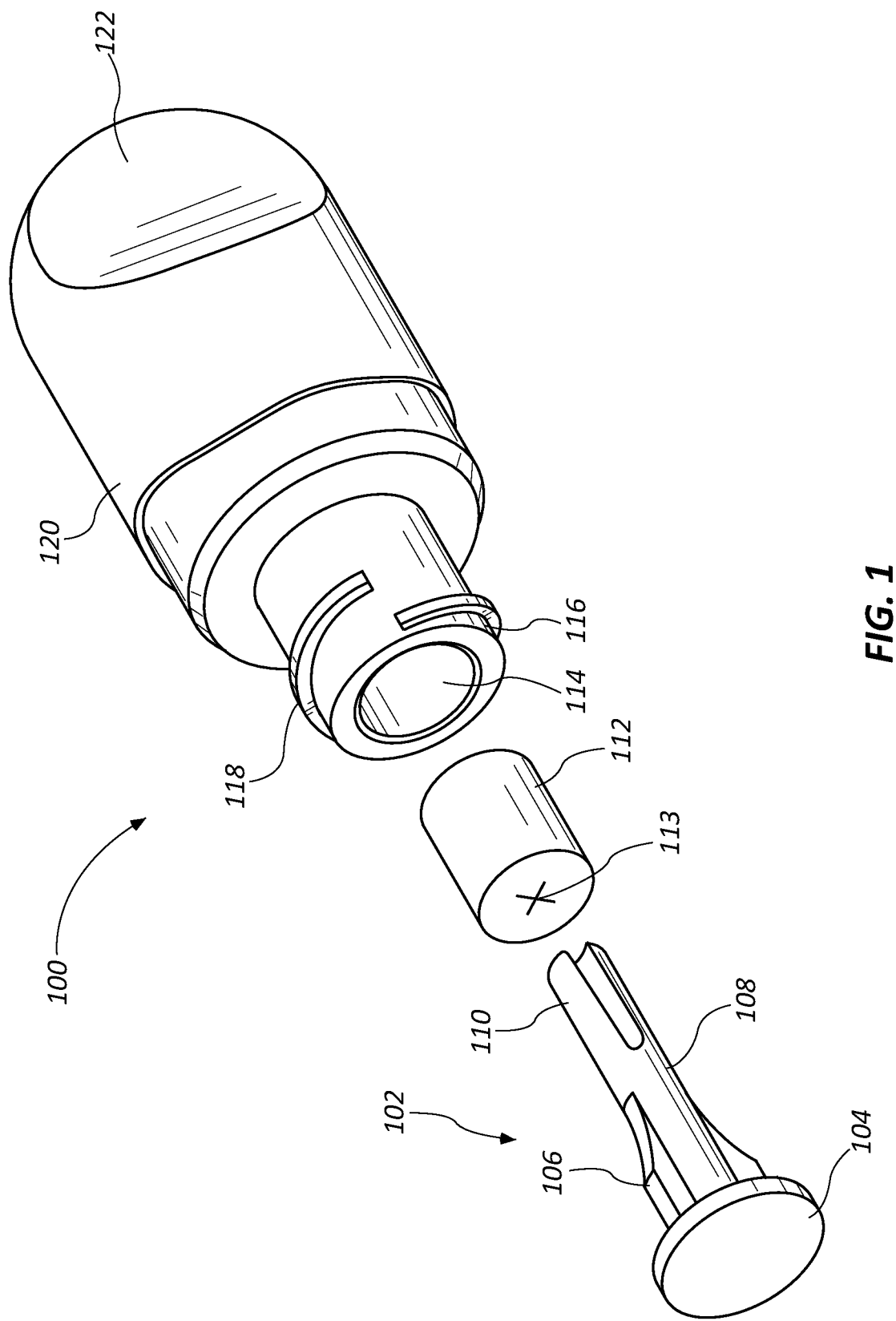
FIG. 1 depicts a simplified exploded view of certain components of a medical connector cap.

Patients undergoing various treatments may receive a central vascular catheter. Exposure of such catheters to foreign bodies increases the risk of catheter-related bloodstream infections. Infections associated with central venous catheters are categorized as either central-line associated bloodstream infections or catheter-related bloodstream infections. These infections can increase hospital costs and length of stay. The costs to hospitals and the health care system from these infections are substantial in terms of both morbidity and resources expended.

In the detailed description, reference is made to the accompanying drawings which form a part hereof and in which are shown, by way of illustration, specific embodiments of the disclosure. These embodiments are described in sufficient detail to enable those of ordinary skill in the art having the benefit of this disclosure to practice the present disclosure, and it is to be understood that other embodiments may be utilized, and that structural, logical, and electrical changes may be made within the scope of the disclosure. From the following descriptions, it should be understood that components of the embodiments as generally described and illustrated in the figures herein could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

In this description, specific implementations are shown and described only as examples and should not be construed as the only way to implement the present disclosure unless specified otherwise herein. It will be readily apparent to one of ordinary skill in the art having the benefit of this disclosure, for example, that the various embodiments of the present disclosure may be practiced with numerous types and forms of medical connectors. The devices and methods described herein could be useful in a number of environments that employ conduits or connectors, for example, the present disclosure may be practiced in any situation that uses at least one connector with a luer end.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

The phrases "connected to" and "coupled to" refer to any form of interaction between two or more entities, including mechanical, electrical, magnetic, electromagnetic, fluid, and thermal interaction. Two components may be connected or coupled to each other even though they are not in direct contact with each other. For example, two components may be coupled to each other through an intermediate component.

The directional terms "proximal" and "distal" are used herein to refer to opposite locations on a medical device. The proximal end of the device is defined as the end of the device closest to the end-user when the device is in use by the end-user. The distal end is the end opposite the proximal end, along the longitudinal direction of the device, or the end furthest from the end-user.

Referring in general to the following description and accompanying drawings, various embodiments of the present disclosure are illustrated to show its structure and method of operation. Common elements of the illustrated embodiments may be designated with similar reference numerals. Accordingly, the relevant descriptions of such features apply equally to the features and related components among all the drawings. Any suitable combination of the features, and variations of the same, described with components illustrated in FIG. 1, can be employed with the components of FIG. 2, and vice versa. This pattern of disclosure applies equally to further embodiments depicted in subsequent figures and described hereinafter. The figures presented are not meant to be illustrative of actual views of any particular portion of the actual structure or method, but are merely idealized representations employed to more clearly and fully depict the present disclosure defined by the claims below.

One embodiment of the present disclosure comprises a cap for a medical connector. The medical connector may have a luer connector. The cap may further comprise a disinfecting agent. In some embodiments the cap comprises a chamber containing the disinfecting agent. When an end-user attaches the cap comprising the disinfecting agent to the luer connector it applies the disinfectant to the open end of the luer connector. The open end of the cap is configured to connect to a medical connector such as a luer connector. In some embodiments the cap is configured to engage with a female luer connector, and in other embodiments the cap is configured to a male luer connector. For example, the cap may be configured with threads to engage a medical connector such as a male or female luer connector. In some embodiments these threads are configured with a hard stop to prevent an end-user from over rotating the cap. Additionally or alternatively, the threads may be configured to provide sufficient rotation of the cap with respect to a connector to dispense an adequate amount of antiseptic fluid to provide effective disinfection.

The cap may comprise a chamber which has a chamber inner lumen. Within the cap chamber the cap may further comprise a reservoir and an insert. The insert is disposed in the chamber lumen and comprises a first end which is shaped to engage with the open end of a medical connector such as a luer connector. This shape may be dome shaped, a frusto-conical shape, or any other shape which may seal or partially seal the open end of a medical connector to reduce fluid entering the lumen of the medical connector while maximizing the flow of fluid around the insert and the outer surfaces of the medical connector.

In some embodiments the cap is configured to facilitate alignment of the insert with the open end of a medical connector. For example, the insert may be disposed within the cap such that threads of the cap tend to align the insert and a medical connector during coupling of the cap and medical connector. The insert may thus tend to engage flush with the open end of a luer connector. In some embodiments the insert may engage substantially perpendicular to the open end of the luer so that the entire circumference of the open end of the luer connector engages substantially simultaneously with the insert. Engaging substantially simultaneously around the entire circumference of the open end of the luer connector may, in turn, reduce or minimize an antiseptic fluid from flowing into the inner luminal space of the luer connector when it engages with the cap.

The insert may also comprise an annular gap that allows an antiseptic fluid to flow around the insert and interact with the surface of the dome shaped first end of the insert during coupling of a cap and a medical connector. As the cap engages with the medical connector radial expansion of the insert may tend to reduce or eliminates this gap reducing or eliminating the amount of antiseptic fluid which can flow around the insert and interact with the medical connector.

Some caps within the scope of this disclosure may be configured to hold 45 pounds per square inch (PSI) of pressure.

The insert may further comprise a second end which is configured to deform when an end-user, such as a health care worker, engages the cap onto a medical connector. As the medical connector, such as the luer connector, is engaged with the cap the open end of the luer connector exerts axial force against the insert. In some embodiments, the insert second end deforms radially as the insert moves axially. The inner walls of the cap chamber may limit the degree the insert second end is able to deform under this axial force. In some embodiments, when the end-user disengages the cap from the luer connector, the insert second end begins to assume its original shape. In this way the insert may move like a spring axially within the cap chamber. When the insert springs back into its original shape it may thus maintain an axial force against the luer connector open end until the luer connector fully disengages from the cap. As the cap is disengaged in this manner the seal or partial seal is maintained between the insert first end and the open end of the luer connector, minimizing the amount of fluid that is able to enter the open end of the luer connector. This second end of the insert may be thought of as a controlled-deformation segment and serves to provide axial force against the medical connector which has been engaged with the cap. In some embodiments the insert second end may comprise external ribs that contact protrusions on the internal sidewall of the cap chamber. The cap is reusable, for example, configured with an insert that is able to deform and spring back into its original shape multiple times, or the cap may be configured as a single use device. The cap second end is further configured to be grasped comfortably and securely by an end-user, such as a health care worker.

In some embodiments the cap chamber further comprises a reservoir configured to absorb fluid, such as disinfectant antiseptic fluid. In some embodiments the reservoir is polyester urethane foam. In some embodiments the polyester urethane foam has a density of between 0.5 and 4 lbs/ft3. In some embodiments the polyester urethane foam has a density of between 1 and 3 lbs/ft3. In some embodiments the polyester urethane foam has a density of 2 lbs/ft3. In some embodiments the reservoir surrounds the insert. In alternative embodiments the reservoir is in a hollow portion of the insert. In some embodiments the reservoir is axially distal to the insert, in other words further from the open cap first end. In some embodiments the reservoir is axially proximal to the insert, in other words closer to the open cap first end. In some embodiments the reservoir is in contact with the insert first end. In some embodiments the reservoir is in contact with the insert second end.

Various materials are within the scope of this disclosure. For example, the insert may be comprised of various polymeric and/or elastomeric materials, including silicones, isoprene, neoprene, Santoprene, and so forth. The reservoir may comprise various foam materials, including polyester urethane foam as discussed above. The reservoir may also comprise an elastomeric material, including elastomers including pores or other structures capable of absorbing a liquid antiseptic agent. The reservoir may be a non-particulate elastomer configured to reduce or minimize breakdown of the reservoir that may result in particles within the cap or connector. Embodiments wherein the insert comprises a hollow portion or void with no separate component was a reservoir (such as embodiments wherein a void within an elastomeric insert is configured to act as a reservoir for an antiseptic fluid) are also within the scope of this disclosure.

The cap chamber may contain a disinfectant, such as an antiseptic. In some embodiments this antiseptic may be an antiseptic fluid such as isopropyl alcohol, hydrogen peroxide, chlorhexidine gluconate, iodophor, povidone iodine, or any other suitable antiseptic. In some embodiments the antiseptic is not fluid but in the form of disinfectant beads, such as hydrogel beads, disinfectant foam, or a loaded polymer. In some embodiments the antiseptic is sequestered in the cap chamber within a first closed compartment by a breakable seal, such as a foil seal. This foil seal will stay intact until an end-user engages the cap with a medical connector which then may exert axial pressure on the cap insert. Alternatively, a foil seal may be disposed across the cap chamber such that an end-user can peel off or otherwise remove the foil seal prior to use. The cap insert may then deform, exerting radial force which can then break the seal holding the antiseptic, releasing it into the cap chamber. In this way, the antiseptic is released and surrounds the insert and the outer surfaces of the medical connector while minimizing the amount of antiseptic that enters the luer connector open end which is loosely sealed by the cap insert first end. In some embodiments the antiseptic is soaked into the reservoir, and when the cap insert is pushed axially it compresses the reservoir, releasing the antiseptic into the chamber and similarly surrounding the insert and the outer surfaces of the medical connector. In some embodiments the antiseptic fluid is both in an absorbent reservoir and sequestered in a breakable seal within the cap chamber inner lumen.

In some embodiments when the end-user disengages the cap from the medical connector, the insert returns to its original shape, which increases the volume within the cap chamber. As the insert returns to its original shape the reservoir will expand, increasing the volume of fluid, such as antiseptic fluid, the reservoir can hold. As the reservoir expands it creates a vacuum or partial vacuum acting on the fluid, thus tending to draw in and absorb the fluid which had been surrounding the insert and the outer surfaces of the medical connector. In this way as the cap is disengaged from the medical connector the amount of fluid in contact with the outer surface of the medical connector decreases, which serves to further reduce the amount of fluid that enters the open end of the medical connector as it is fully disengaged from the cap and the insert first end.

In some embodiments the cap insert may be configured to store the antiseptic within the insert. For example, the insert may be hollow with side apertures to permit the antiseptic agent to flow out of the insert when axial force is exerted on the insert from the end-user attaching a medical connector to the cap. In some embodiments the insert first end may inhibit flow of fluid, such as an antiseptic fluid into the lumen of an engaged medical connector while allowing flow to specific regions on or in the medical connector. In some embodiments the insert is made of a single material. In alternative embodiments the insert first end is made of material different from the insert second end. In some embodiments the insert first end is reinforced to reduce deformation when axial force is applied to the insert when an end-user attaches a medical connector to the cap. In some embodiments the cap is configured with radial protrusions to maintain the insert in the cap chamber.

In some embodiments the method of capping a medical connector with a cap, as described above, is disclosed herein. The end-user may obtain a cap, as described above. If a foil seal is present, the end-user may peels off a foil seal from an end of the cap to open the cap chamber. The end-user may then connect the cap to the open end of the medical connect and twist either the cap to fully engage the cap on the connector or the connector to fully engage the cap. The cap will then disinfect, as described above, the outer surface of the medical connector while minimizing the amount of disinfectant that enters the open end of the medical connector. In some embodiments the cap may be configured with threading to engage the medical connector. In some embodiments these threads, or an end of these threads, are configured with a hard stop to prevent the end-user from over rotating the cap on the medical connector. In some embodiments the cap is configured to engage with a female luer connector. In alternative embodiments the cap is configured to engage with a male luer connector. In some embodiments the end of the cap is sealed with a sterile seal which is removable by the end-user just before it is attached to the medical connector.

In some embodiments the means for minimizing medical connector infections is provided by applying a cap, as described above, to a medical connector. The cap applies an antiseptic agent to a medical connector. In some embodiments, the cap has engagement means to attach to a male luer connector. In some embodiments, the cap comprises the means for limiting or minimizing the flow of antiseptic in the cap chamber as the end-user engages the open end of a medical connector with the cap, while at the same time maximizing the flow of antiseptic to the outer surface of the medical connector. In some embodiments the cap comprises an insert in the chamber, the insert comprising the means to exert axial force against the open end of the medical connector as the cap is both engaged and disengaged with the medical connector. In some embodiments the cap is configured with a means of maintaining the insert in the cap chamber.

FIG. 1 depicts a simplified exploded view of various components of a medical connector cap 100. The cap 100 has a cap first end 116 which comprises an opening 114 and a second end 122 configured to be grasped securely and comfortably by an end-user. A cap body 120 is between the cap first end 116 and the second end 122. In the illustrated embodiment, the cap first end 116 is configured to be attached to a male luer connector and further comprises ridges 118 which serve as threads to engage the male luer connector. The cap 100 comprises an insert 102 and a reservoir 112. The insert 102 comprises an insert first end 104 configured to engage and seal or partially seal the open end of a male luer connector. In some embodiments, the insert first end 104 of the insert 102 may comprise a shape configured to seal or partially seal against a portion of a connector, such as a luer connector. For example, in the illustrated embodiment, the insert first end 104 of the insert 102 comprises a dome or curved shape, configured to seal or partially seal against a luer connector. As also described above, other shapes, such as frusto-conical shapes, are within the scope of this disclosure. Further, the insert first end 104 of the insert 102 may be configured to partially conform to the shape of a portion of the luer to facilitate sealing. In some embodiments the insert 102 is disposed within the cap 100 such that the ridges 118, in threaded engagement with the luer, tend to align the cap 100 and the luer before the insert first end 104 engages the luer. Thus, the cap 100 may be configured such that the insert first end 104 is substantially perpendicular to the open end of the luer (not depicted) during coupling of the cap 100 and a luer. In some embodiments insert reinforcements 106 are configured to align or maintain the alignment of the insert first end 104 within (and with respect to) the cap 100.

The insert 102 also comprises an insert body 108 between the insert first end 104 and an insert second end 110. In this embodiment the insert second end 110 is configured to deform under axially applied pressure. In this embodiment the insert first end 104 is reinforced with the insert reinforcement 106 to reduce deformation of the insert first end 104 and the insert body 108 under axially applied pressure. In the depicted embodiment, the reservoir 112 comprises a reservoir hole 113 through which the insert second end 110 and the insert body 108 may be pushed. The insert first end 104 further serves to limit the distance the insert 102 can be pushed through the reservoir hole 113. The insert reinforcement 106 may in some embodiments be configured to further limit the position the insert 102 takes within the reservoir 112.

Figure 2A:
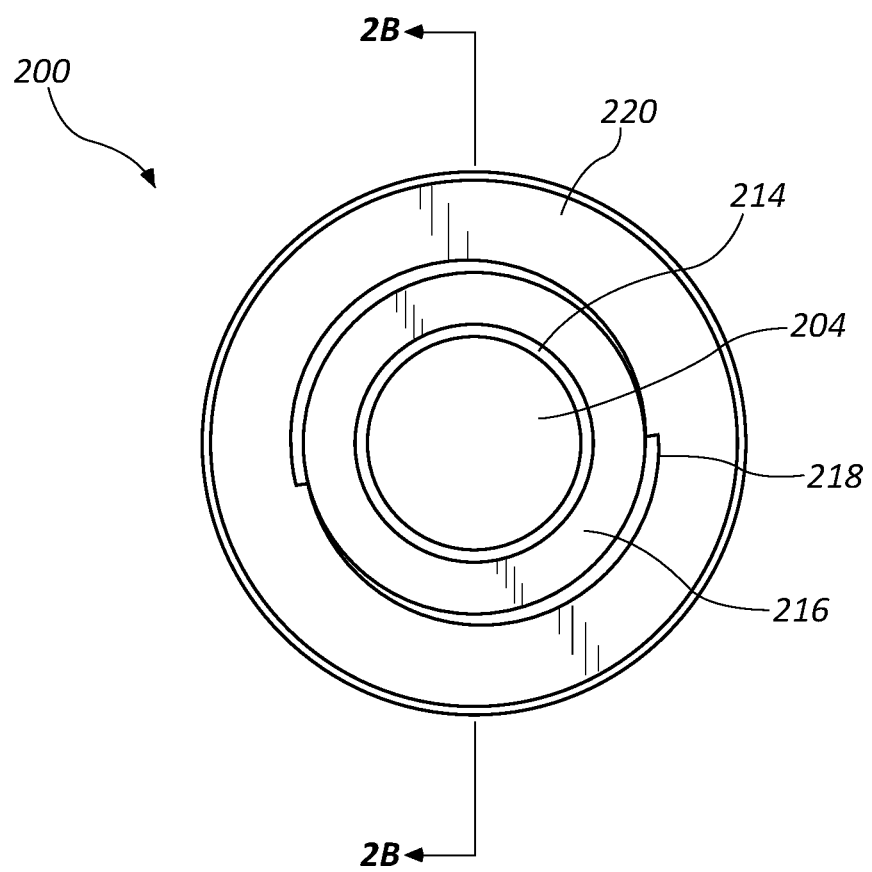
FIG. 2A depicts a simplified end view of certain components of a medical connector cap.

FIG. 2A depicts an end view of another embodiment of a cap 200 that resembles the cap 100 described above in certain respects. Accordingly, like features are designated with like reference numerals, with the leading digits incremented to "2." For example, the embodiment depicted in FIGS. 2A-2B includes a cap body 220 that may, in some respects, resemble the cap body 120 of FIG. 1. Relevant disclosure set forth above regarding similarly identified features thus may not be repeated hereafter. Moreover, specific features of the cap 200 and related components shown in FIGS. 2A-2B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the cap 200 and related components depicted in FIGS. 2A-2B. Any suitable combination of the features, and variations of the same, described with respect to the cap 100 and related components illustrated in FIG. 1 can be employed with the cap 200 and related components of FIGS. 2A-2B, and vice versa. This pattern of disclosure applies equally to further embodiments depicted in subsequent figures and described hereafter, wherein the leading digits may be further incremented.

The cap 200 comprises the cap body 220 and a cap first end 216. The cap first end 216 comprises a cap opening 214. The cap first end 216 is further configured to engage a male luer connector with threads 218. An insert first end 204 is visible through the cap opening 214. FIG. 2A also indicates plane A-A through which a cross-section of the cap 200 is taken and shown in FIG. 2B.

Figure 2B:
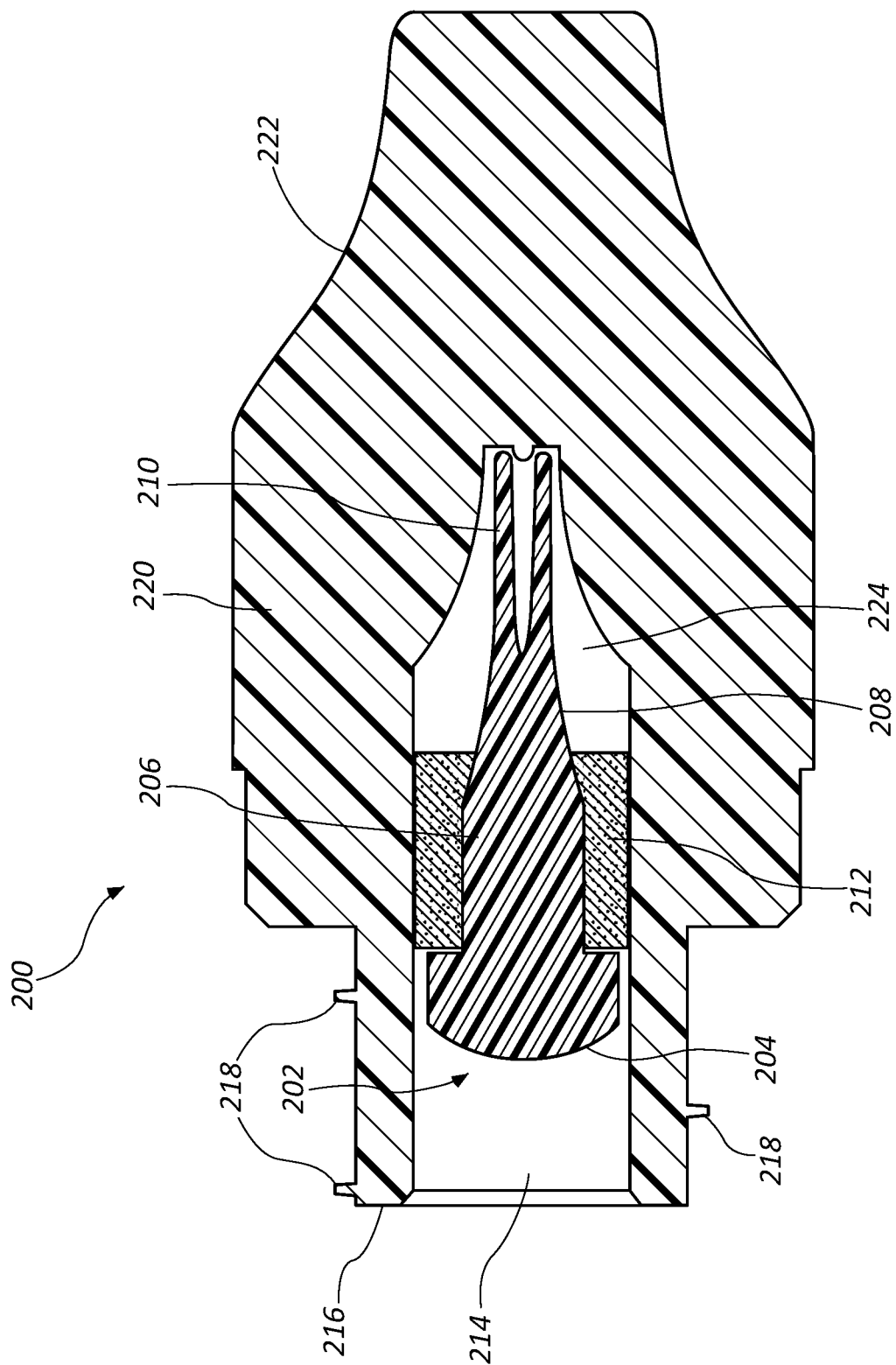
FIG. 2B depicts a simplified cross-section view of certain components of the medical connector cap of FIG. 2A, taken through plane A-A.

As noted above, FIG. 2B depicts a cross-section view of the cap 200 through plane A-A of FIG. 2A. With reference to FIGS. 2A-2B, the cap 200 illustrated therein comprises the cap first end 216, the cap body 220, and a cap second end 222. The cap first end 216 comprises protrusions 218 which serve as threading to engage with a male luer connector. The cap first end 216 further comprises the cap opening 214. The cap 200 also comprises a cap chamber 224. In the illustrated embodiment, the cap chamber 224 comprises an inner lumen which contains an insert 202 and a reservoir 212. The insert 202 comprises the insert first end 204 configured to engage with the open end of a medical connector. The insert 202 further comprises an insert body 208 and an insert second end 210. The insert body 208 comprises an insert reinforcement 206 to reduce deformation of the insert 202 under axially applied pressure. The insert second end 210 is configured to deform under axially applied pressure. In this embodiment the insert second end 210 comprises two prongs which will bow outward radially until they come into contact with the cap chamber's 224 inner walls.

Figure 3A:
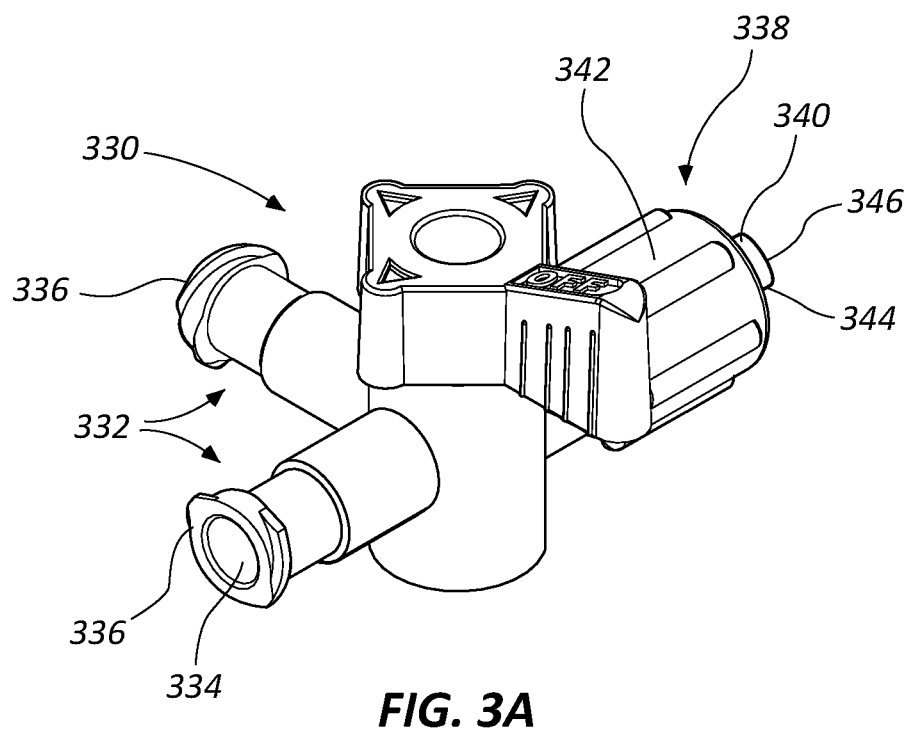
FIG. 3A depicts a simplified perspective view of a medical connector.
Figure 3B:
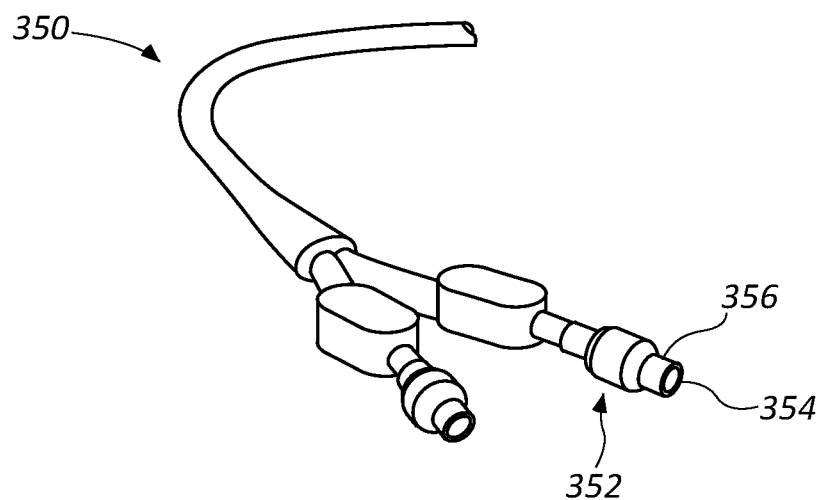
FIG. 3B depicts a simplified perspective view of another embodiment of a medical connector.

FIGS. 3A and 3B depict two examples of medical connectors. FIG. 3A depicts a perspective view of a medical connector hub 330. The hub 330 has both a male luer connector 338 and two female luer connectors 332. The female luer connector 332 comprises a first end 336 and an opening 334. The male luer connector 338 comprises a threaded engagement member 342, a male luer connector body 340, and a male luer connector first end 344. The male luer connector first end 344 comprises a male luer opening 346. FIG. 3B depicts a medical connector 350 which comprises a female luer connector 352 with a first end 356. The female luer connector 352 first end 356 comprises a first opening 354.

Figure 4A:
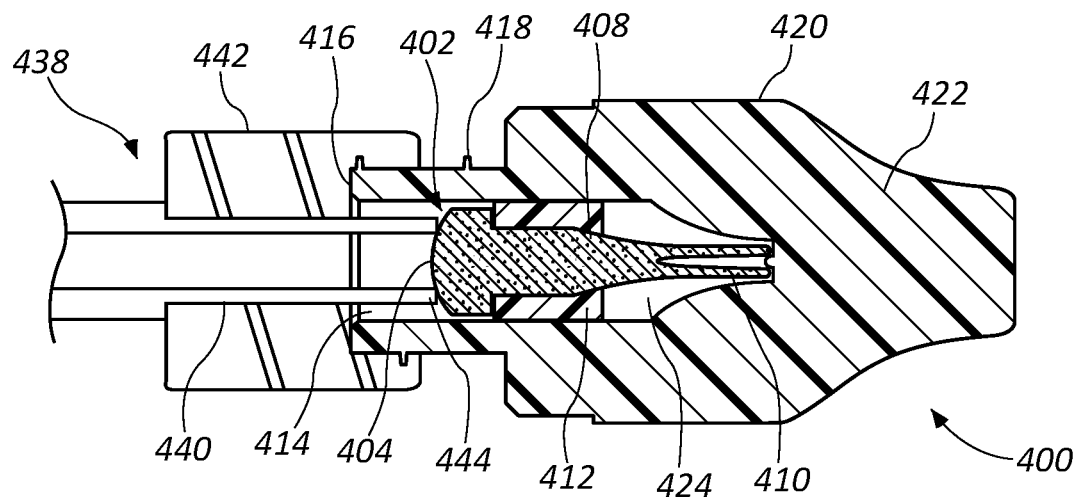
FIG. 4A depicts a simplified cross-section view of certain components of a medical connector cap engaging with certain components of a medical connector, in a first configuration.
Figure 4B:
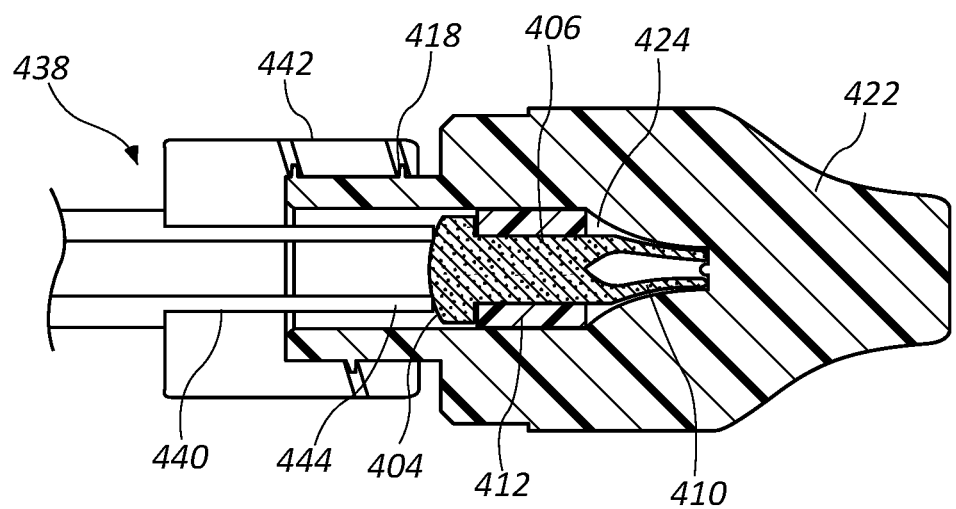
FIG. 4B depicts a simplified cross-section view of certain components of the medical connector cap and medical connector of FIG. 4A in a second configuration.

FIGS. 4A and 4B depict cross-section views of a cap 400 engaging a male luer connector end 438, in first and second configurations, respectively. The medical connector such as the male luer connector end 438 is inserted so that a male luer connector body 440 is inserted into a cap opening 414. The end-user will slide the male luer connector body 440 into the cap opening 414 until a male luer open end 444 comes into contact with an insert first end 404. A male luer threaded engagement member 442 slides around a cap first end 416 to begin to engage with cap protrusions 418 which serve as threading. An insert reinforcement 406 and insert body 408 as well as a cap body 420 and cap second end 422 are also indicated in the figures.

In the first configuration, shown in FIG. 4A, the end-user has not yet exerted enough axial force on an insert 402 to push it axially into a cap chamber 424 enough to deform an insert second end 410. In the second configuration, shown in FIG. 4B, the end-user has exerted enough axial force on the insert 402 to deform the insert second end 410. The male luer threaded engagement member 442 is thus in position to engage the threading via the cap protrusions 418 and further tighten the cap 400 onto the male luer connector end 438 which will exert additional axial force on the insert 402. As the insert 402 is forced down into the cap chamber 424 the insert second end 410 deforms, which may result in the decrease of the cap chamber 424 available volume and the compression of a reservoir 412. An antiseptic (not depicted) may then be forced out of the reservoir 412 (for example due to the decrease in the volume of the reservoir 412) into this remaining cap chamber 424 volume and would be exposed to the outer surface of the male luer open end 444 and the male luer connector body 440. As the male luer connector end 438 is further tightened onto the cap 400 it may be configured to limit the amount of antiseptic which spills outside of the cap opening 414. In other words, the reservoir 412 may act like a sponge, absorbing antiseptic liquid when the reservoir 412 is uncompressed and releasing antiseptic liquid into the cap chamber 424 as the reservoir 412 is compressed. Backing the cap 400 off the luer may allow the reservoir to return to an uncompressed configuration and reabsorb liquid antiseptic disposed in the cap chamber 424.

Figure 5:
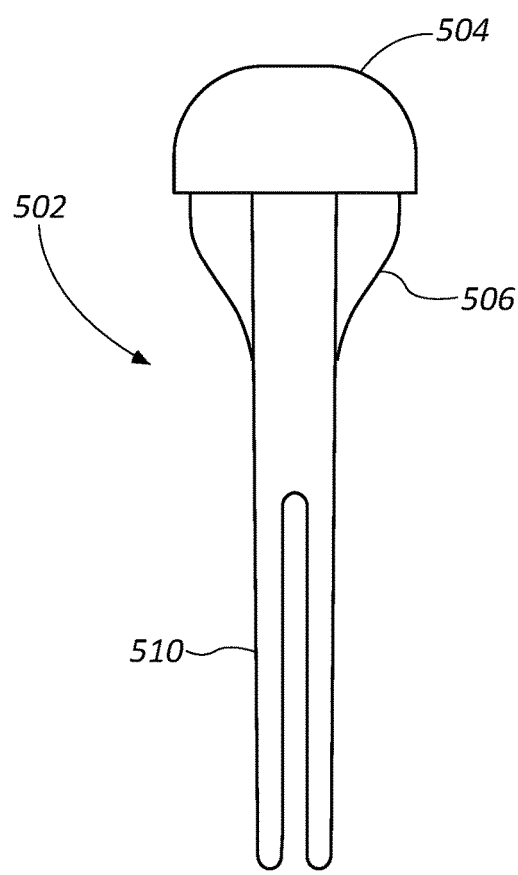
FIG. 5 depicts a simplified side view of a portion of a medical connector cap.

FIG. 5 depicts a side view of a cap insert 502. The insert 502 comprises an insert first end 504 configured and shaped to engage and seal or partially seal a medical connector open end. The insert 502 further comprises a reinforcement 506 configured to reduce deformation of the insert 502 near the insert first end 504. An insert second end 510 is configured to deform under axially applied pressure. The insert 502 of FIG. 5 is shown in a generally uncompressed configuration.

Figure 6:
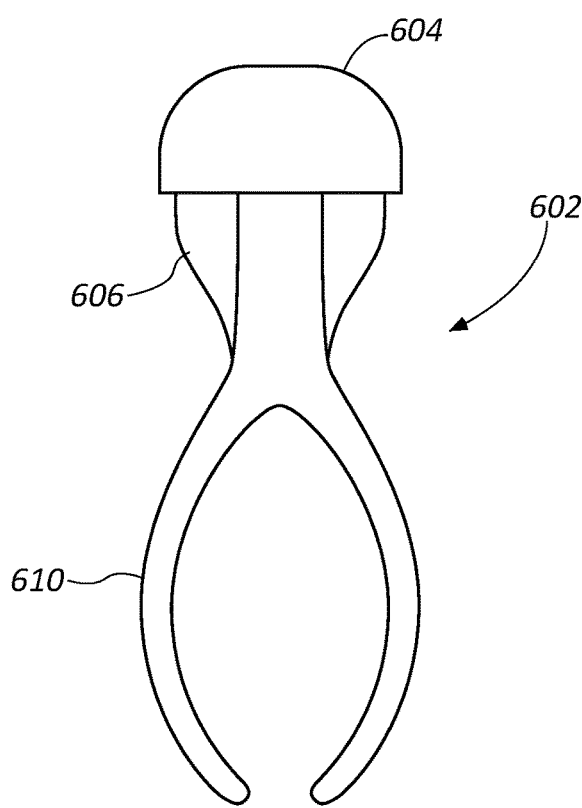
FIG. 6 depicts a simplified side view of a portion of another embodiment of a medical connector cap.

FIG. 6 depicts a side view of a cap insert 602 shown after axially applied pressure has deformed an insert second end 610. In other words, as compared to the uncompressed configuration of the insert 502 of FIG. 5, FIG. 6 illustrates an analogous insert 602 in a compressed configuration. An insert first end 604 remains in its original shape and thus resists angular misalignment of the insert first end 604. The insert first end 604 is reinforced with an insert reinforcement 606. In other embodiments the insert first end 604 resists deforming under axially applied pressure while the insert second end 610 deforms because the insert first end 604 is made up of more rigid material than the insert second end 610.

Figure 7:
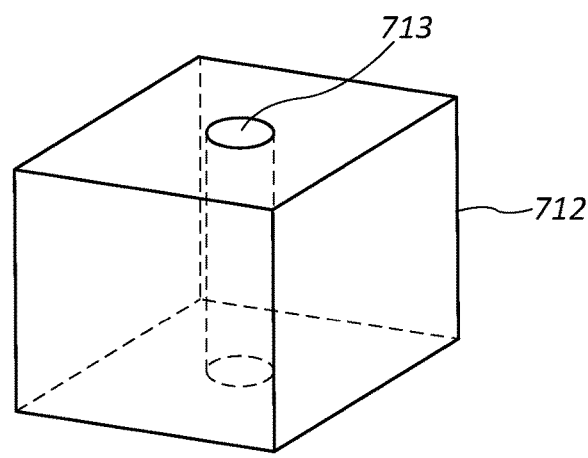
FIG. 7 depicts a simplified perspective view of a portion of another embodiment of a medical connector cap.

FIG. 7 depicts a perspective view of one embodiment of a reservoir 712. This embodiment of the reservoir 712 is a cube, and the reservoir 712 comprises an opening 713 through which an insert, such as the insert 502, may be placed.

Figure 8A:
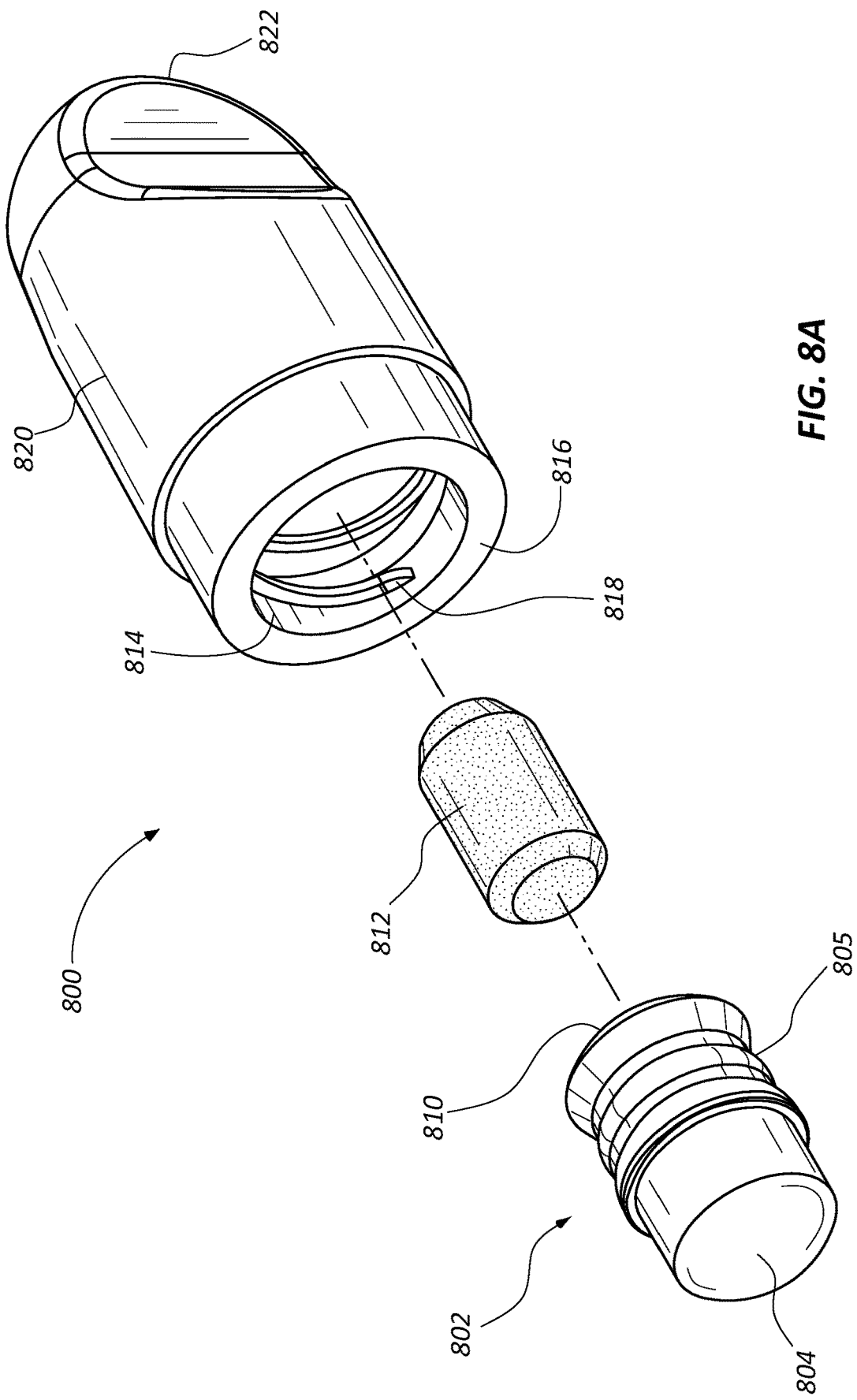
FIG. 8A depicts a simplified exploded view of certain components of a medical connector cap.

FIG. 8A depicts a simplified exploded view of various components of a medical connector cap 800. The cap 800 has a cap first end 816 which comprises a cap opening 814 and a cap second end 822 configured to be grasped by an end-user. A cap body 820 is between the cap first end 816 and the cap second end 822. In the illustrated embodiment, the cap first end 816 is configured to be attached to a female luer connector and further comprises ridges 818 which serve as threads to engage the female luer connector. The cap 800 comprises an insert 802 and a reservoir 812. The insert 802 comprises an insert first end 804 configured to engage and seal or partially seal the open end of a female luer connector (not depicted).

The insert first end 804 of the insert 802 may be dome shaped, with a hemispherical shape to engage and seal or partially seal the open end of a female luer connector (not depicted). Additionally or alternatively, the insert first end 804 of the insert 802 may be configured to partially conform to the shape of a portion of the luer to facilitate sealing. In some embodiments the insert 802 is disposed within the cap 800 such that the ridges 818, in threaded engagement with a luer, tend to align the insert 802 and the luer before the insert first end 804 of the insert 802 engages the open end of the luer. Additionally, in some embodiments the insert 802 comprises an insert second end 810 which is open and configured to accept a reservoir such as the reservoir 812 within the insert 802.

In some embodiments, the cap 800 is configured such that there is an annular gap 805 between the insert 802 and the cap 800 when the insert 802 is unconstrained. This annular gap 805 may allow an antiseptic fluid to flow around the insert 802, for example, from the reservoir 812 adjacent the insert second end 810 of the insert 802. Thus, the annular gap 805 may allow antiseptic fluid from the reservoir 812 to interact with the insert first end 804 and then come into contact with the luer end (not depicted) during coupling of a luer and the cap 800. In some embodiments when the luer cap is partially or fully engaged with the cap 800 a compressive force exerted on the insert 802 by the luer may cause the insert 802 to radially expand, thus reducing or closing the annular gap 805. This, in turn, may reduce or eliminate the antiseptic fluid flow around the insert 802, which may limit excess antiseptic fluid from entering the luer end.

Figure 8B:
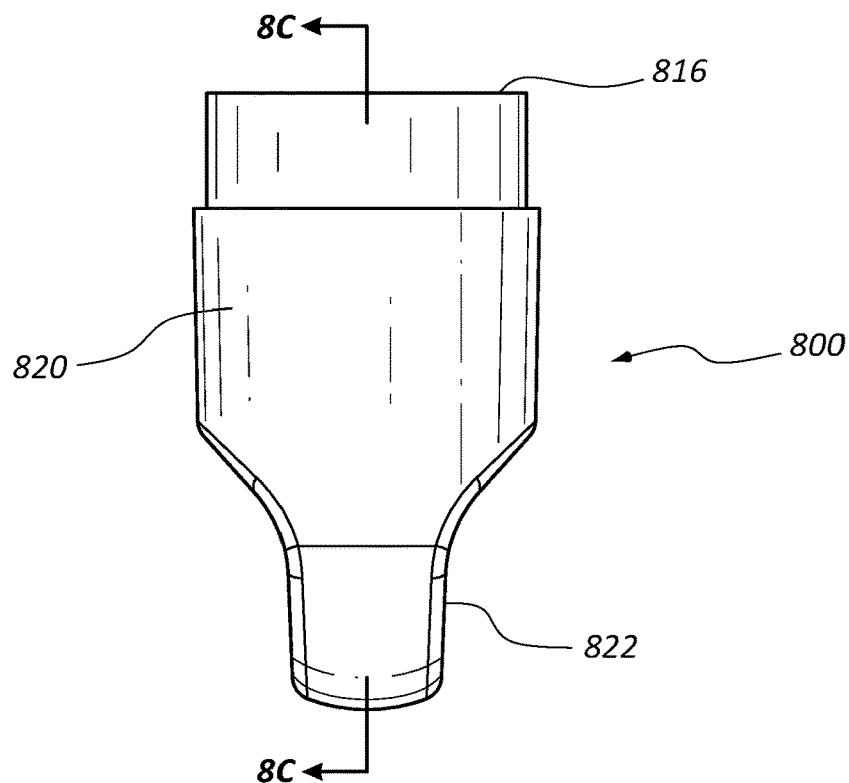
FIG. 8B depicts a simplified side view of certain components of a medical connector cap.

FIG. 8B depicts a side view of the cap 800. The cap 800 comprises the cap body 820 and the cap first end 816. The cap first end 816 comprises an opening (not depicted). The cap first end 816 may be configured to engage a luer or other medical connector. The cap second end 822 may be configured to be grasped by an end-user. Line 8C of FIG. 8B indicates the plane of the cross-section depicted in FIG. 8C.

Figure 8C:
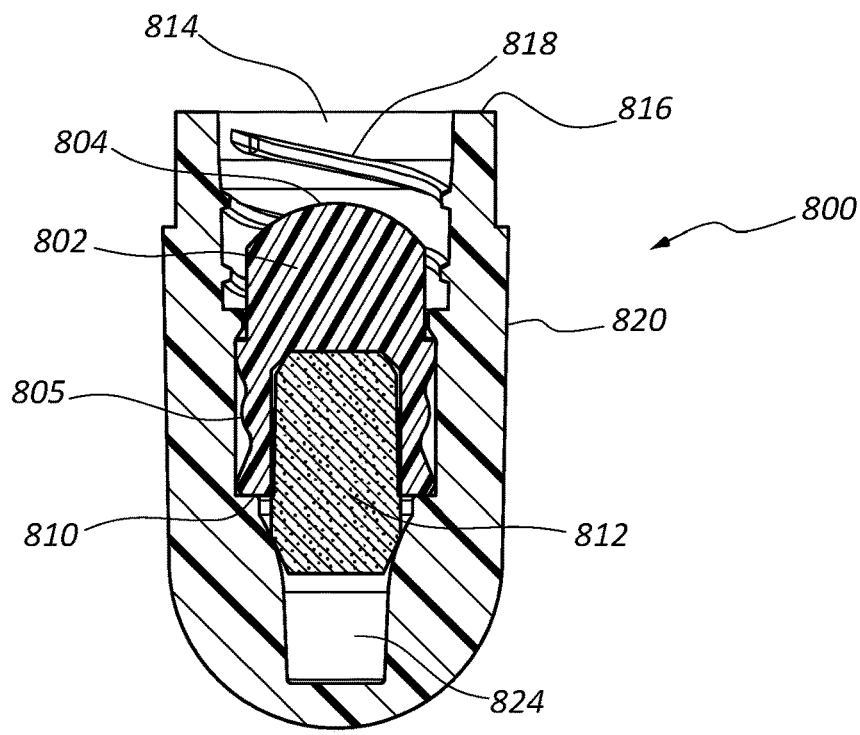
FIG. 8C depicts a simplified cross-section view of certain components of the medical connector cap of FIG. 8B taken through plane 8C.

FIG. 8C depicts a cross-section of the cap 800. The cap body 820 and cap first end 816 and indicated in this figure. In the illustrated embodiment, the cap first end 816 comprises the cap opening 814. Further, the ridges 818 within the cap opening 814 may be configured as threads for engagement with a luer connector (not depicted).

As shown in FIG. 8C, the cap 800 may also comprise the cap chamber 824. The cap chamber 824 defines an inner lumen which contains the insert 802 and the reservoir 812. Again, the first end 804 of the insert 802 is positioned and configured to engage with the open end of a medical connector such as a luer when the cap 800 is coupled to a medical connector. The insert second end 810 of the insert 802 may be configured to accommodate the reservoir 812 inside, or partially inside, the insert 802. As noted above, the insert 802 and cap 800 may define the annular gap 805. In some embodiments an antiseptic fluid (not depicted) is disposed within the cap chamber 824. The reservoir 812 may absorb some or all of the antiseptic fluid.

Figure 9A:
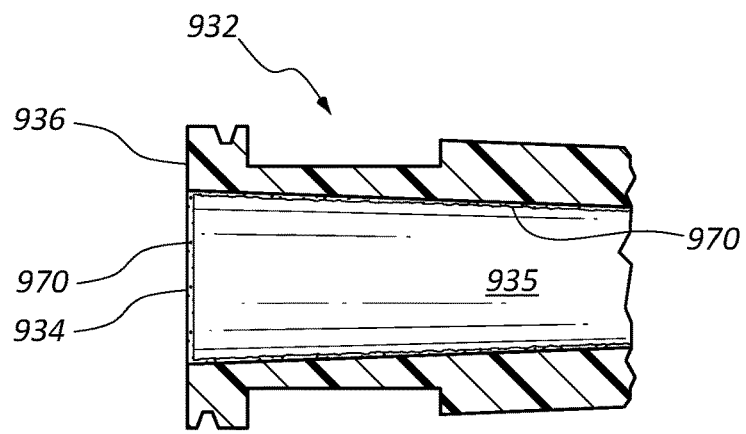
FIG. 9A depicts a simplified cross-section view of certain components of a female luer connector.
Figure 9B:
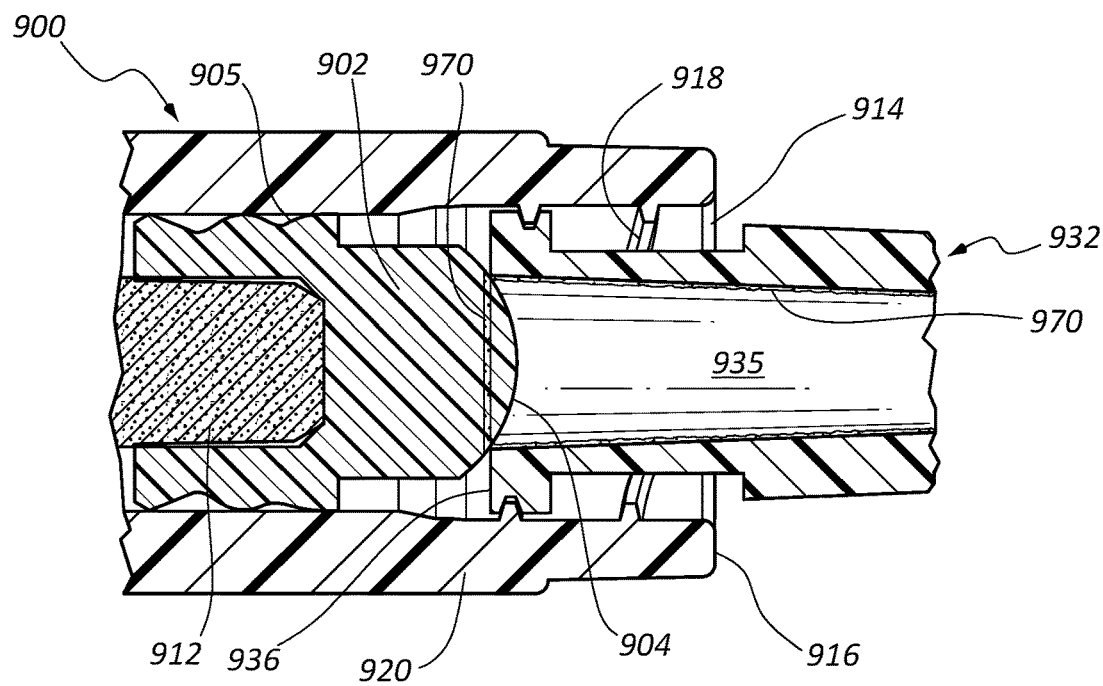
FIG. 9B depicts a simplified cross-section view of certain components of a medical connector cap engaged with a female luer connector.
Figure 9C:
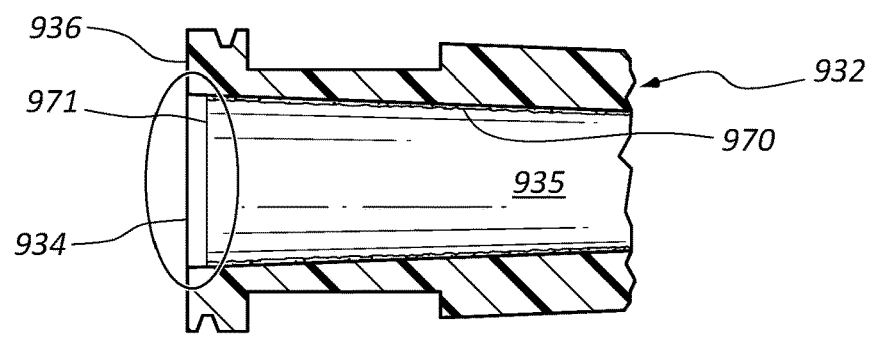
FIG. 9C depicts a simplified cross-section view of certain components of a female luer connector.

FIGS. 9A-9C depict a female luer connector 932 being connected to a cap body 920. FIG. 9A depicts a cross-section of the luer connector 932 with a female luer connector first end 936 comprising an opening 934. FIG. 9B depicts the cap body 920 engaging with the luer connector 932. A first cap end 916 of the cap body 920 comprises an opening 914 into which the luer connector 932 can be engaged. Ridges 918 disposed within the opening 914 are configured as threads to engage the female luer connector first end 936. In the illustrated embodiment, an insert 902 has a dome shaped first end 904 which is configured to engage with the female luer connector first end 936. An annular gap 905 is disposed between the insert 902 and the cap body 920. The insert 902 may also partially receive and/or surround a reservoir 912. As further detailed in Example 1, below, FIGS. 9A-9B also depict the deposition of a tungsten powder 970 on an inner luminal surface 935 of the female luer connector first end 936 and around the circumference of the opening 934.

FIG. 9C depicts a cross-section of the female luer connector first end 936 after it has been disengaged from a cap 900, according to the procedure outlined in Example 1. As compared to the connector as depicted in FIGS. 9A-9B, the tungsten powder 970 generally remains on the inner luminal surface 935 after disengagement of the female luer connector first end 936 from the cap 900. As illustrated in FIG. 9C, in some instances the tungsten powder 970 may be displaced by the first end 904 of the insert 902 when coupled as shown in FIG. 9B. As explained in Example 1, the position of the tungsten powder 970 in FIG. 9C illustrates how the insert 902 and reservoir 912 may limit ingress of antiseptic fluid into the female luer connector first end 936.

Kits that include a medical connector cap are also within the scope of this disclosure. For example, a kit may include any of the devices described above. The kit may also include other elements, such as instructions for using the devices. Kits may additionally or alternatively include (1) male luer connector caps; (2) female luer connector caps; (3) double-ended luer connector caps; (4) sterile gloves; (5) sterile barrier; (6) antiseptic swabs; and (7) sterile gauze, among other potential elements.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

While the disclosure is susceptible to various modifications and implementation in alternative forms, specific embodiments have been shown by way of non-limiting example in the drawings and have been described in detail herein. However, it should be understood that the disclosure is not intended to be limited to the particular forms disclosed. Rather, the disclosure includes all modifications, equivalents, and alternatives falling within the scope of the disclosure as defined by the following appended claims and their legal equivalents.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

Example 1

Disinfecting caps for open female connectors were tested with stopcock connectors to observe alcohol ingress into the lumen of the stopcock connector. Testing did not show alcohol ingress but reflected evidence of the insert protruding for up to 1 mm into the lumen of the connector. As discussed above, FIGS. 9A-9C schematically illustrate the components of this Example. Three luer connector/cap assemblies were tested. For this example, the inserts 902 were made from Santoprene 8281-55MED. The reservoir 912 was composed of polyester urethane foam measuring 0.2 inches in diameter and having a height of 0.3 inches. 175 µl of 70% isopropyl alcohol was dispensed into the cap 900, and the insert 902/reservoir 912 assembly was inserted into the cap 900. The resulting assembly was analogous to the assembly of the embodiment shown in FIG. 8C.

A layer of the tungsten powder 970 was dusted into the inner luminal surface 935 of the luer connector 932 to act as the contrast agent, as the tungsten powder 970 would get disrupted when it encountered alcohol during testing of coupling and uncoupling of the luer connector 932 and the cap 900.

Luer connectors 932 dusted with a tungsten powder 970 (in the configuration shown in FIG. 9A) were mounted onto a luer post and placed in a 3D CT scanner for imaging. The luer connectors 932 were then assembled with the caps 900 as shown in FIG. 9B and exposed to x-rays which was then followed by disassembly and a last round of imaging.

The caps 900 were found to maintain contact with the opening 934 of the luer connector 932 as the insert 902 in the cap 900 deformed to maintain pressure at the insert 902—the opening 934 interface. This seal prevented alcohol from contact with the inner luminal surface 935 of the luer connector 932. Tungsten particles were observed to be displaced (as shown in FIG. 9C) around the circumference of the opening 934. This displacement can be attributed to the physical disturbance caused by the insert 902 that protruding into luer connector 932 to prevent alcohol ingress.

We claim:

1. A cap for a medical connector, the cap comprising:
   a first end comprising a first opening configured to connect a medical connector;
   a chamber disposed in the cap;
   a reservoir disposed at least partially within the chamber; and
   an insert disposed at least partially in the chamber, the insert comprising a dome shaped first end and a second end configured to deform during use,
   wherein the second end is further configured to return at least partially back to its original shape during use.

2. The cap of claim 1, wherein the chamber contains a disinfectant.

3. The cap of claim 2, wherein the disinfectant is an antiseptic fluid.

4. The cap of claim 3, wherein the antiseptic fluid is selected from the group consisting of: isopropyl alcohol, hydrogen peroxide, chlorhexidine gluconate, iodophor, and povidone iodine.

5. The cap of claim 3, wherein the insert first end is configured to limit fluid flow into a connector lumen when the insert first end is in contact with the connector; and wherein the insert first end is reinforced to limit deformation of the insert first end.

6. The cap of claim 2, wherein the disinfectant is selected from the group consisting of: disinfectant beads, disinfectant foam, and disinfectant loaded polymer.

7. The cap of claim 6, wherein the disinfectant beads are hydrogel beads.

8. The cap of claim 2, wherein the reservoir is compressed when the insert second end deforms.

9. The cap of claim 8, wherein the reservoir expands and tends to absorb the disinfectant in the reservoir when a connector is disconnected from the first opening, and
wherein the insert first end maintains at least a partial seal on the open end of the connector while the connector is being disconnected.

10. The cap of claim 8, the chamber further comprising a first closed compartment containing the disinfectant, the closed compartment configured to open and release the disinfectant when the insert second end deforms.

11. The cap of claim 1, wherein the reservoir is absorbent.

12. The cap of claim 1, wherein the reservoir is a polyester urethane foam.

13. A method of capping a medical connector, the method comprising:
connecting a cap to and open end of a medical connector;
contacting a first end of an insert disposed within the cap with the medical connector;
deforming a second end of the insert such that the second end of the insert provides a force to maintain contact between the first end of the insert and the medical connector,
wherein the second end is configured to deform away from an original shape and return at least partially back to the original shape during use; and
disinfecting the open end of the medical connector while minimizing introduction of disinfectant inside the open end of the medical connector.

14. The method according to claim 13, wherein the cap comprises threads configured to prevent an end-user from over rotating the cap.

15. The method according to claim 13, wherein the disinfectant is an antiseptic fluid.

16. The method according to claim 13, wherein the disinfectant is selected from the group consisting of: disinfectant beads, disinfectant foam, and disinfectant loaded polymer.

17. The method according to claim 13, further comprising compressing an absorbent reservoir within the cap to release antiseptic fluid.

18. The method according to claim 17, wherein the reservoir is a polyester urethane foam.

19. The method according to claim 17, further comprising absorbing a portion of the antiseptic fluid in the reservoir by uncompressing the reservoir.

* * * * *

UNITED STATES PATENT AND TRADEMARK OFFICE
CERTIFICATE OF CORRECTION

PATENT NO. : 10,603,481 B2  
APPLICATION NO. : 15/874505  
DATED : March 31, 2020  
INVENTOR(S) : Avula et al.

Page 1 of 1

It is certified that error appears in the above-identified patent and that said Letters Patent is hereby corrected as shown below:

In the Claims

Column 13, Line 17 Claim 13 reads, ". . . cap to and open . . ." which should read, ". . . cap to an open . . ."

Signed and Sealed this  
Eleventh Day of August, 2020

Andrei Iancu  
*Director of the United States Patent and Trademark Office*